United States Patent [19]

Love et al.

[11] Patent Number: 4,726,889
[45] Date of Patent: Feb. 23, 1988

[54] PROCESS AND APPARATUS FOR CONDUCTING ELECTROPHORESIS AND TRANSFER

[75] Inventors: Jack D. Love, Wheaton; Michael T. Elliott, Gaithersburg; Patricia L. Morgan, Hyattsville, all of Md.

[73] Assignee: Oncor, Inc., Gaithersburg, Md.

[21] Appl. No.: 825,921

[22] Filed: Feb. 4, 1986

[51] Int. Cl.[4] ..................... G01N 27/28; G01N 27/26
[52] U.S. Cl. ............................... 204/182.8; 204/299 R
[58] Field of Search ............ 204/182.8, 299 R, 182.9, 204/182.6, 301; 935/76, 77, 78

[56] References Cited

U.S. PATENT DOCUMENTS

| | | | |
|---|---|---|---|
| 3,407,133 | 10/1968 | Oliva et al. | 204/299 R |
| 3,755,121 | 8/1973 | Schlutz | 204/299 R X |
| 3,773,646 | 11/1973 | Mandle et al. | 204/299 R |
| 4,151,065 | 4/1979 | Kaplan et al. | 204/299 R |
| 4,181,594 | 1/1980 | Rizk et al. | 204/299 |
| 4,391,688 | 7/1983 | Hamelin | 204/180 |
| 4,415,418 | 11/1983 | Turre et al. | 204/182.8 |
| 4,452,901 | 6/1984 | Gordon et al. | 204/182.8 X |
| 4,455,370 | 6/1984 | Bartelsman et al. | 935/78 |
| 4,589,965 | 5/1986 | Kreisher | 204/299 R X |

FOREIGN PATENT DOCUMENTS 0161635 11/1985 European Pat. Off.
8702132 4/1987 PCT Int'l Appl.
2147609 5/1985 United Kingdom.

OTHER PUBLICATIONS

M. Peferoen et al, "Vacuum-Blotting: a New Simple and Efficient Transfer of Proteins from Sodium Dodecyl sulfate-Polyacrylamide Gels to Nitrocellulose", Febs. Letters, 1982, vol. 145, No. 2, pp. 369-371.

Zaitsev, I. Z. et al., "Vacuum Transfer at DNA to Filters for Detecting Inter-Individual Polymorphism by the Southern Blotting Hybridization Method", Byull. Eksp. Biol. Med., 1983, 96(10), p. 846, (Abstract only).

E. M. Southern, "Detection of Specific Sequences Among DNA Fragments Separated by Gel Electrophoresis", Journal of Molecular Biology, (1975), 98, 503-517.

M. Bittner et al., "Electrophoretic Transfer of Proteins and Nucleic Acids from Slab Gels to Diazobenzyloxymethyl Cellulose or Nitrocellulose Sheets", Analytical Biochemistry 102, 459-471, (1980).

Bethesda Research Laboratories, Inc., "Catalogue & Reference Guide", Aug. 1983, p. 51.

Primary Examiner—John F. Niebling
Assistant Examiner—John S. Starsiak, Jr.
Attorney, Agent, or Firm—Burns, Doane, Swecker & Mathis

[57] ABSTRACT

An apparatus for carrying out horizontal gel electrophoresis for separation and subsequent vacuum-assisted transportation of macromolecules to a support membrane to facilitate detection. The entire procedure is conducted in one cartridge. A method for conducting electrophoresis and subsequent vacuum-assisted transfer using the apparatus of the present invention is also disclosed.

26 Claims, 11 Drawing Figures

PROCESS AND APPARATUS FOR CONDUCTING ELECTROPHORESIS AND TRANSFER

FIELD OF THE INVENTION

This invention relates to processes and apparatus for carrying out horizontal gel electrophoresis for separation and subsequent vacuum assisted transportation of macromolecules to a support membrane to facilitate detection.

BACKGROUND OF THE INVENTION

The process known as electrophoresis involves the migration of charged molecules through a suitable retarding medium under the influence of an electric field. Generally, the compounds of higher molecular weight migrate at a slower rate through the medium than do the compounds of lower molecular weight. Devices have been provided previously for carrying out electrophoresis. An example of such a device is U.S. Pat. No. 4,415,418 in which a tray is provided with a raised platform at the center. Removable partitions are placed in the tray at opposite ends of the platform, and a conventional electrophoresis gel is poured over the platform to form a thin layer. When the gel has cooled, the partitions are removed. A comb is provided to form wells across the surface of the gel. Substances that are to be subjected to electrophoresis are delivered into each of the wells, and the tray is at least partially filled with an electrolyte buffer. Electrodes are positioned at each end of the tray and a sufficient voltage difference is applied to the electrodes to cause migration of the molecules of the substance in the wells across the length of the gel, separated according to their molecular weight. After electrophoresis, the gel is removed from the original casting tray, and placed in a dish containing depurination solution. Approximately thirty minutes later this solution is poured out by tipping the dish toward one edge while the gel is held with the fingers. It is important to use great care during this procedure to prevent the gel from breaking because there is no gel support structure and subsequent processing is possible only with an integral gel. A denaturation solution is then added to the dish and incubation is continued for approximately thirty minutes. Again, the solution is carefully poured off. Then neutralization buffer is added and incubation is continued for thirty additional minutes.

In accordance with conventional techniques, transfer of the nucleic acids is accomplished by placing a piece of filter paper, which is as wide as and longer than the gel, on a platform which is suspended above a solution of 10× saturated saline citrate buffer (SSC). The ends of the filter paper are long enough to hang off the ends of the platform and dip into the 10× SSC. Thus, the filter paper acts as a wick to absorb the SSC solution. The gel is removed from the dish and placed on top of the filter paper saturated with 10× SSC. Next, a piece of membrane filter paper which is the same size as the gel is saturated with 10× SSC and placed on top of the gel. The nucleic acids are eventually bound to the membrane filter paper. Another piece of saturated filter paper, the same size as the gel, is placed on top of the membrane. The entire layered unit is then smoothed to remove any air bubbles that may exist between the gel and the filter paper. Finally, a stack of paper towels, the same size as the gel, is positioned on top of the layered unit.

Over a period of about 12 to 16 hours, the 10× SSC solution is drawn up through the gel by capillary action and the nucleic acids are transferred out of the gel into the membrane above. The paper towels absorb the excess buffer and provide the force for capillary action. At the end of the transfer period, the entire layered unit is disassembled and the membrane is removed for hybridization. This technique is described in an article Southern, E., "Detection of Specific Sequences Among DNA Fragments Separated by Gel Electrophoresis," . *J. Mol. Biol.*, 98:503 (1975).

Although the trays such as the one described in U.S. Pat. No. 4,415,418 are convenient for carrying out electrophoresis, they are not suitable for situations where a large number of samples must be tested in a relatively short period of time.

Therefore, the prior art uses a tedious multi-step, multi-apparatus process for preparing nucleic acid fragments for subsequent hybridization. Four steps are generally undertaken to achieve preparation of the sample for hybridization. Electrophoresis was previously described. Depurination removes purine bases from nucleic acids. Denaturation involves separating the strands of nucleic acids and breaks down the depurinated nucleic acids into suitable size to allow eventual transfer of the fragments out of the gel. Transfer involves allowing the fragments to go out of the gel onto the porous membrane.

OBJECTS OF THE INVENTION

It is the principal object of the present invention to provide one apparatus wherein the steps of electrophoresis, depurination, denaturation and transfer to a membrane may all be carried out.

It is an object of the present invention to standardize and simplify the electrophoresis and transfer techniques to facilitate applications of molecular biology.

It is a further object of the present invention to develop an apparatus for electrophoresis and transfer which offers considerable time and cost savings.

Another object of the present invention is to avoid the difficulties generally associated with prior art methods and apparatus with respect to handling the gel and further processing.

SUMMARY OF THE INVENTION

In accordance with the present invention, nucleic acid fragments such as DNA and RNA may be prepared for subsequent hybridization using the process and apparatus of this invention. The process and apparatus are particularly useful for detection of gene rearrangements, restriction fragment polymorphisms and restriction fragment patterns. The process and apparatus enables rapid screening of tissue specimens and body fluids for the presence of infectious viruses such as Human Papilloma virus, for typing B-cell and T-cell monoclonal populations, and for screening patients for the development of cancer or other disease states.

Thus, the apparatus of the present invention combines in a single unit means for conducting electrophoresis and transfer, and includes a tray having opposite side walls, opposite end walls and a bottom wall. There is a central platform in the tray, with a vacuum chamber between the platform and the bottom wall. The platform surface is pervious to liquid. A liquid reservoir is provided adjacent each of the end walls and electrophoresis electrodes are mounted in the reservoirs. A conduit is provided for transferring liquid into and out of the tray. The tray is covered by a lid. The apparatus is adapted to perform electrophoresis and transfer without removing the gel from the tray.

The process of the present invention is performed by placing a transfer membrane on a porous platform in a tray. The gel is placed on the membrane. Samples are deposited in spaced wells in the gel. An electrophoresis buffer is pumped into the tray to cover the gel and the electrodes and an electric potential is applied between the electrodes. After the electrophoresis step, depurination and denaturation are carried out while the gel remains in the tray. During the denaturation step, the liquid is drawn through the porous membrane to cause the displaced samples to be transferred from the gel to the membrane.

DETAILED DESCRIPTION OF THE DRAWINGS

A preferred embodiment of the invention is illustrated in the accompanying drawings, in which:

FIG. 7 is a cross-sectional view of the lid along the line 7—7 in FIG. 6;

FIG. 8 is a cross-sectional view of the lid along the line 8—8 in FIG. 6;

FIG. 9 is a detail plan view of the tray with the bridge installed;

FIG. 10 is a front elevational view of the tray with the bridge installed as in FIG. 9; and FIG. 11 is a cross-sectional view of the bridge and tray along the line 11—11 in FIG. 9.

DETAILED DESCRIPTION

Figure 1:
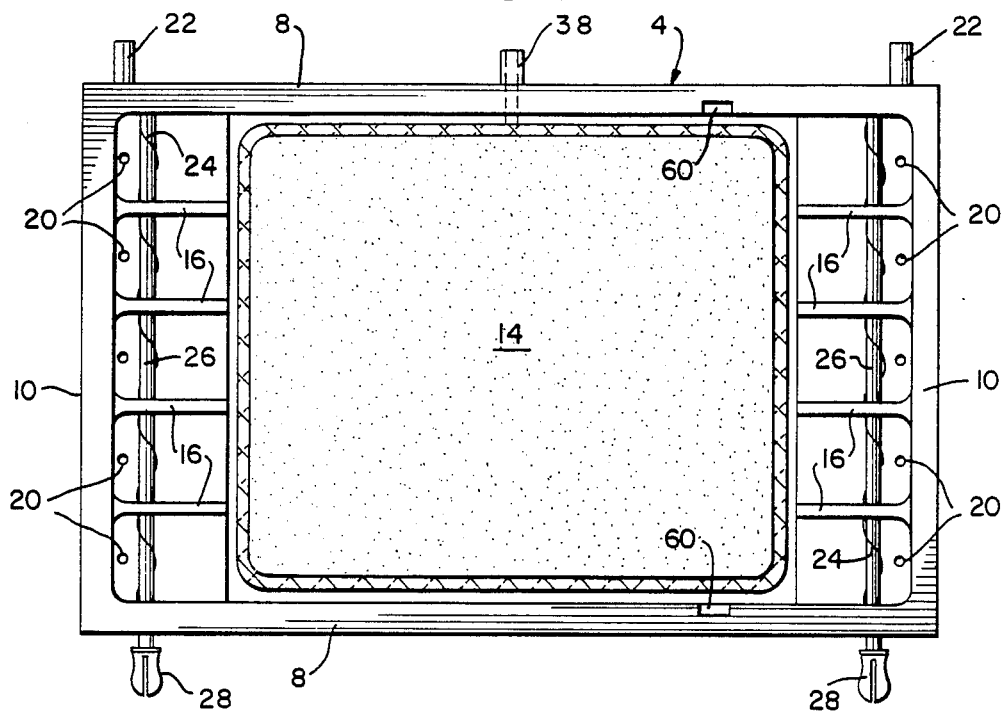
FIG. 1 is a top plan view of the electrophoresis transfer tray in accordance with this invention, with the lid removed.
Figure 2:
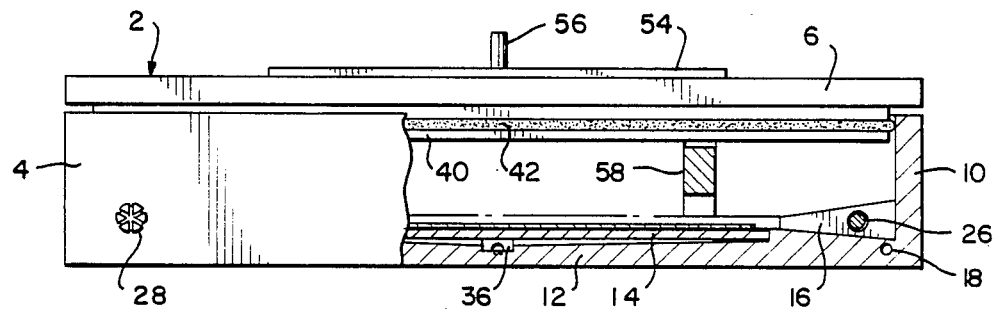
FIG. 2 is a side elevational view of the cartridge of this invention, partially in cross-section.

Referring to FIGS. 1 and 2, a cartridge 2 is used for carrying out the electrophoresis and transfer processes of this invention. The cartridge 2 includes a tray 4 and a lid 6. Tray 4 is preferably composed of polyvinyl chloride or Delrin, a resin which is a registered trademark of E. I. duPont de Nemours & Co. Inc.; however, any material which has good dimensional stability for fabrication and non-electrically conductive and which is chemically compatible with the intended use is suitable. The tray 4 has opposite side walls 8, end walls 10 and a bottom wall 12. A support surface 14 is provided at the center of the tray. The bottom wall 12 adjacent the end walls 10 slopes downwardly, as shown in FIG. 2 away from the support surface 14. A plurality of webs 16 extend inwardly from the end walls 10. The webs facilitate insertion of the gel without tearing. The webs also align the gel thereby assuring proper orientation of the gel in the electric field.

Figure 4:
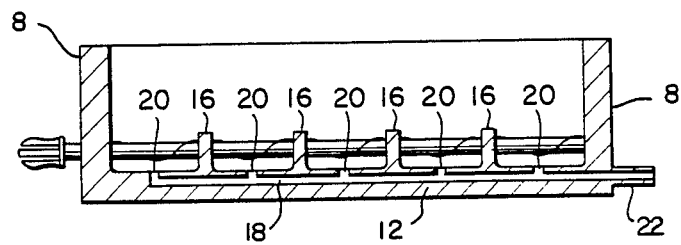
FIG. 4 is a cross-sectional view of the tray along the line 4—4 in FIG. 3.

As shown in FIGS. 2 and 4, a transverse passage 18 is provided in the bottom wall 12 and ports 20 communicate with the passage 18 to allow the circulation of fluid into and out of the tray. A tubing fitting 22 is provided on the side wall 8. An identical passage 18 is provided at the opposite end of the tray (FIG. 1) and has corresponding ports 20 and a tube fitting 22.

Electrodes are provided at each end of the tray. The electrode 24 is in the form of a thin wire, preferably of platinum, which is wrapped on an insulated rod 26. The rod is supported in aligned holes in the webs 16. The electrode 24 extends through the side wall 8 and is connected with an electrical contact element 28 which is adapted to be connected to a source of electric potential.

Figure 5:
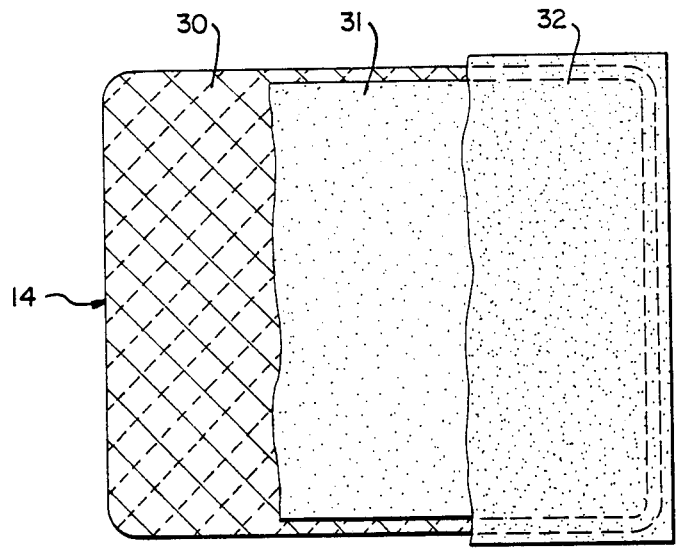
FIG. 5 is a detail view of the plate on which the membrane and gel are superimposed.

The support surface 14 is formed of a porous plate 30 (FIG. 11). Any porous plate is suitable, however, a plate made of a porous polyethylene is preferred. The porous plate should be about 30% to 85% open to sufficiently pull water. As shown in FIG. 5, the plate 30 has parallel score lines on each side which are perpendicular, so that small holes through the plate are formed at the inner section of the score lines. Of course, any suitable porous plate could be substituted for the plate 30. A porous membrane 31 rests on the plate 30. Membrane 31 must have properties such that it is optimum for binding of vacuum assisted transported DNA fragments. Membrane 31 is preferably comprised of nylon or nitrocellulose such as a nylon membrane comprised of about 0.2 to 1.2 micron porosity. However, any fluid-permeable membrane which is sufficient to bind nucleic acids would be suitable.

Figure 3:
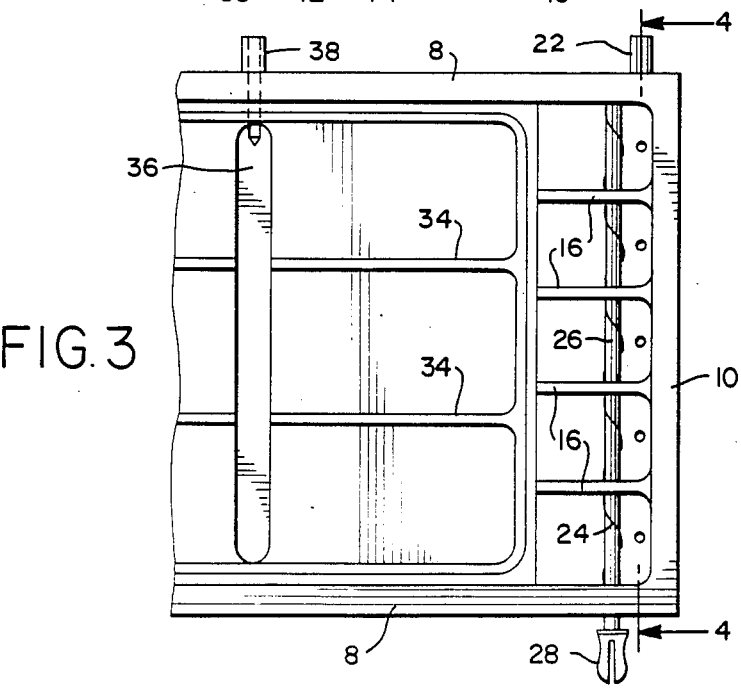
FIG. 3 is a detail top plan view of the tray with the perforated plate removed.

A gel is cast on a separate tray. The gel can be agarose, polyacrylamide, mixed agarose/polyacrylamide or any other material suitable for the separation of macromolecules in an electric field. Generally, 0.7% w/v agarose is used. The gel 32 is then placed on the surface of the membrane 31 in a suitable mold and then transferred to the tray 4 where it is superimposed on the plate 30, as shown in FIG. 5. A vacuum chamber is provided beneath the plate 30, as shown in FIGS. 2 and 3. The chamber includes a pair of ridges 34 extending outwardly from a central channel 36. A tubing fitting 38 extends through the side wall 8 and communicates with the channel 36. The fitting 38 is adapted to be connected by tubing to a suitable vacuum pump. The opposite ends of the gel 32, when placed in the tray 4, abut the ends of the webs 16, as shown in FIG. 11. The side edges of the gel 32 are positioned by engagement with the side walls 8 of the tray. The membrane 31 is spaced inwardly from the edge of the plate 30 along all four sides of the plate, so that the vacuum that is applied beneath the plate will tend to hold the ends and sides of the gel against the plate 30. If additional means are required to keep the gel 32 from floating in the fluid, a band or tube 39 (FIGS. 9 and 11) may be applied across the surface of the gel at each end. The ends of the tube 39 are secured in the side walls 8.

Figure 6:
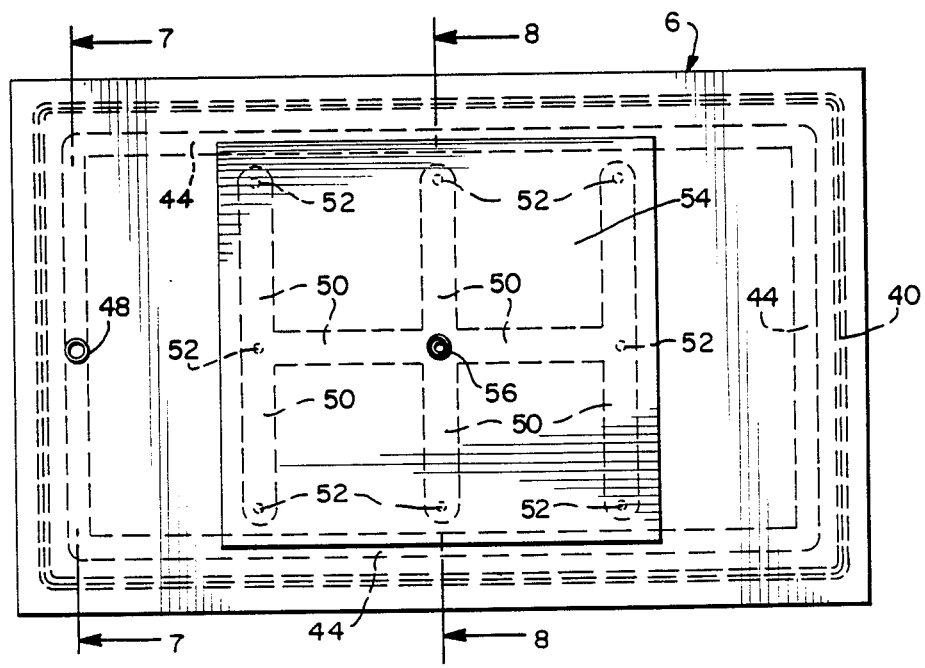
FIG. 6 is a top plan view of the lid for the cartridge.

As shown in FIG. 6, the lid 6 has a shoulder 40 which extends around the perimeter of the lid and engages the inside surface of the side walls 8 and the end walls 10. A sealing gasket 42 is retained within a groove in the shoulder 40. The gasket 42 prevents the leakage of fluid from the interior of the cartridge. A gas bubble channel 44 is formed in the interior of the lid 6 and extends along the end walls and side walls of the tray. The channel portion at the right side of FIG. 6 is more shallow than the groove at the left side of FIG. 6, and the grooves extending along the side walls 8 progressively increase in depth from the right end to the left end as viewed in FIG. 6. This arrangement of the grooves causes the gas bubbles to migrate progressively toward an outlet port 46 through the lid 6. The outlet port has a tube fitting 48 through which the gas bubbles can escape.

The central portion of the lid 6 has a plurality of grooves 50 formed in the top side of the lid. As shown in FIGS. 6 and 8, ports 52 extend from the bottom of the grooves to the lower surface of the lid so that fluid can pass from the grooves 50 into the interior of the cartridge when the lid is in place. A cover plate 54 encloses the grooves 50 and a tube fitting 56 allows liquid to be conducted through the plate 54 into the interior of the grooves 50.

In order to enable samples to be delivered into the wells formed in the gel layer 32, a bridge 58 is provided. The bridge aids in directing the operator to the correct well for sample filling thus making it easier to fill the well. The bridge is received in vertical slots 60 in each of the side walls 80 at a position that is aligned with the wells that are molded in the gel layer. A black strip may be positioned near the wells to aid in visualizing the wells during sample loading. The bridge 58 includes funnel-shaped passages 62 in a shape to receive the tip of a pipette for delivering the samples into the wells formed in the gel. As shown in FIG. 10, arches 64 are formed in the bridge between the passages 62 to allow fluid circulation between opposite sides of the bridge. If additional recirculation is necessary, the bridge can be removed prior to electrophoresis.

In operation, a gel layer is formed in accordance with conventional practices of a proper size and shape to fit within the tray 4, so that the ends abut the ends of the webs 16 and the sides of the gel fit between the side walls 8 of the tray. Preferably, the gel is cast in a separate tray and has a series of wells molded in the gel layer adjacent one end. The gel 32 is then removed from the casting tray and placed on the flexible permeable membrane 31, so that it occupies the position shown in FIGS. 5, 9 and 11. The sloping top edge of each web 16 aids in guiding the gel into position in the tray 4. A source of electric potential is connected with the electrical connectors 28 and a system for circulating fluid is connected with the tubing fittings 22. An electrophoresis buffer is added to the tray to a depth that fully covers the electrodes 24 and the gel. The bridge 58 is installed in the slots 60 after the gel layer is positioned on the support surface 14. The samples are then delivered into the passages 62 from which they pass into the individual wells. The bridge remains in place when the lid 6 is applied. The electrophoresis buffer is recirculated through the passages 18 by the use of a conventional pump, to provide a fluid current passing over the gel. At the end of electrophoresis, the electrophoresis buffer is then pumped out of the tray and a depurination buffer is pumped into the tray. After a period of time, the depurination buffer is then pumped out of the tray and a denaturation buffer is pumped into the tray. After a suitable elapse of time, the denaturization buffer is withdrawn through the vacuum fitting 38 at a relatively slow rate, which transfers the displaced samples from the gel onto the permeable membrane. As an alternative, water or denaturation liquid may be sprayed onto the surface of the gel through the tube fitting 56 as the liquid is being withdrawn through the tube fitting 38. The lid 6 is then removed and the permeable membrane 31 may be removed from the tray for further processing. The membrane now contains the displaced samples in preparation for hybridization.

The cartridge of this invention has the important advantage that it allows electrophoresis and transfer to occur without having to remove the gel from the tray. At the completion of the operation, the nylon membrane bearing the samples can readily be removed for subsequent treatment.

The electrophoresis apparatus is designed to accommodate either a large number of analytical samples or milligram quantities of fragments for preparative runs. Typically, the number of samples which may be introduced into the cartridge may range from about 5 to 15. Generally, 10 samples plus two controls has been found to be suitable.

The tray 4 and the lid 6 must be compatible with standard electrophoresis and nucleic acid transfer reagents. Typical reagents include up to 3 molar (M) salts, acetic acid, 1 M hydrochloric acid and 0.5 M sodium hydroxide. Many polymers could be suitable for the present invention. Furthermore, in view of the direct current being used during electrophoresis, the tray 4 and lid 6 should not conduct electricity. The lid 6 is preferably plexiglass (acrylic) since a further advantage is obtained with the use of a clear cover since it would allow visual tracking of optional dyes during electrophoresis.

Using one buffer or solution throughout the foregoing procedure is more efficient and economical than using a different buffer or solution during each of the electrophoresis, depurination, denaturation and transfer stages. Alternatively, four separate solutions may be used in the practice of the present invention. For example, during electrophoresis any buffer well-known in the art is suitable such as any solution of a weak acid or base and its salts, such as acetates, borates, phosphates and phthalates, which behave as buffers. Typical compounds used in preparing buffers include acetic acid, phenylacetic acid, sodium acetate, ethylene diamine tetraacetic acid (EDTA), phosphoric acid, boric acid, hydrochloric acid, sodium hydroxide, sodium chloride and the like. During electrophoresis, a buffer comprised of 40 mM tris-acetate, pH 8, 12 mM sodium acetate and 2 mM EDTA, pH 8, is preferred.

During depurination, any solution which chemically assists in depurination or depyrimidination would be useful. These solutions are well-known in the art. A buffer comprised of 0.25 M hydrochloric acid is preferred.

During denaturation, any solution which assists in breaking the hydrogen bonds between the nucleic acid strands is suitable. These solutions are also well-known in the art. For example, water and heat may provide satisfactory results, also formamide or any alkali such as sodium hydroxide or potassium hydroxide. In the present invention a solution of 0.5 M sodium hydroxide is preferred.

As the transfer solution, any solution which allows transfer and binding of the nucleic acid strands to the membrane would be suitable. These solutions are also well-known in the art. Advantageously, in the practice of the present invention the transfer solution is preferably 0.5 M sodium hydroxide, the same as the denaturation solution.

The time periods used in each of the above-described stages may vary over a wide range depending on the processing conditions. For instance, each of electrophoresis, denaturation and depurination may require from about 10 minutes to 5 hours. Useful techniques to decrease the amount of time required for processing include increasing the voltage, using larger ports, selecting the optimum thickness of the gel, different sizes of membranes and the support plate, and the like. A particular advantage of the present process is that the time required for electrophoresis is approximately 40–65% of the typical time required for electrophoresis using prior art apparatus and techniques. A significant time savings is offered by the present invention because of the circulation of fluids, i.e., buffers, through the electrophoresis transfer cartridge, thereby allowing a constant pH and temperature to be maintained during the process. In addition, the geometry of the cartridge results in concentrating the electric field within the gel which also speeds the process.

Furthermore, by maintaining a relatively frequent circulation of the buffer, a smaller volume of buffer is suitable in contrast to the buffer requirements of prior art electrophoresis processes.

The transfer step may require from about 10 minutes to two hours. Generally, about 60 minutes produces adequate results. This step also offers a considerable time savings over prior art transfer techniques. Capillary transfer, for instance, requires about 12 hours, squash blot transfer requires about 3 hours and standard electrotransfer requires about four hours.

A further advantage of the present invention is the time and labor savings that results since the apparatus is a cartridge. The decrease in the number of mechanical steps to be performed by a technician or operator assists in maintaining the accuracy of the procedure since a decrease in the number of necessary steps to be performed also minimizes error.

Other components are useful to achieve the objects of the present invention in addition to the above-described electrophoresis transfer cartridge. For instance, a microprocessor controller may be used to automate electrophoresis and DNA/RNA transfer. Such a controller would control the voltage and time for electrophoresis, the valves for reagents, the pumps to add and remove reagents and the vacuum system for DNA transfer. The electrophoresis transfer cartridge may be connected to a variety of standard laboratory equipment including peristaltic pumps.

The following example is intended to demonstrate one method that may be used to practice the present invention. The following is not intended to limit the invention in any way.

EXAMPLE

Electrophoresis Transfer Process

A 14 cm long×11 cm wide×0.65 cm deep 0.7% w/v agarose gel having a nylon membrane on its bottom surface was placed and aligned in a polyvinyl chloride electrophoresis transfer tray having inside dimensions of 20 cm long×11 cm wide×2 cm deep. A liquid pervious platform or support plate made of porous polyethylene rests on the inside of the tray. Approximately 200 ml of an electrophoresis buffer comprised of 40 mM tris-acetate, 12 mM sodium acetate and 2 mM EDTA was added by hand. Restriction enzyme digested human genomic DNA samples were loaded into the wells and a plexiglass top was placed over the polyvinyl chloride tray. The unit was then plugged into a power supply which was set at 90 volts. The power was turned on. Electrophoresis was allowed to continue for approximately ten minutes. Then the buffer was recirculated at a rate of approximately 25 ml/min for the duration of electrophoresis. Electrophoresis continued for approximately two hours. The power was turned off and the electrophoresis buffer was pumped out.

Approximately 200 ml of a depurination solution comprising 0.25 M hydrochloric acid was pumped into the polyvinyl chloride tray. The solution was allowed to stand for approximately 15 minutes and then the solution was pumped out. Next, approximately 200 ml of a denaturation solution was added to the polyvinyl chloride tray. A vacuum pump was turned on to withdraw fluid through the porous polyethylene plate at about 2 ml/min. This was continued for 60 minutes to allow the DNA to transfer from the gel to the nylon membrane below the gel. The unit was turned off.

While this invention has been illustrated and described in accordance with a preferred embodiment, it is recognized that variations and changes may be made therein without departing from the invention as set forth in the claims.

What is claimed is:

1. Apparatus for conducting electrophoresis and subsequent transfer, comprising:
    a tray having opposite side walls, opposite end walls and a bottom wall;
    platform means in said tray for supporting a gel, said platform means including a support plate that is pervious to liquid;
    said tray and platform means defining a chamber between said plate and said bottom wall;
    electrode means for applying an electric field in said tray between said end walls, said platform means being between said electrode means;
    liquid reservoir means adjacent said end walls;
    conduit means for transferring liquid into and out of said tray; and
    lid means for covering said tray.

2. The apparatus according to claim 1 wherein said liquid reservoir means extends between said side walls and along each end wall and said bottom wall, said conduit means including passages in said tray communicating with said reservoir means whereby liquid is transferred into and out of said tray through said reservoir means.

3. The apparatus according to claim 2 wherein said liquid reservoir means includes a plurality of webs extending inwardly from said end wall toward said platform means, and said electrode means includes an elongated electrode extending through and supported by said webs.

4. The apparatus according to claim 1 including means for applying a vacuum to said chamber, whereby liquid passes through said plate into said chamber upon the application of a vacuum in said chamber.

5. The apparatus according to claim 4 wherein said apparatus includes a porous membrane on said plate, whereby a gel may be superimposed on said membrane and said plate for electrophoresis and transfer of samples from the gel to the membrane.

6. The apparatus according to claim 4 wherein said liquid reservoir means extends between said side walls and along each end wall and said bottom wall and includes a plurality of webs extending inwardly from said end wall toward said pervious plate, said webs terminating at a predetermined distance from said plate, whereby said webs serve as guides for locating the ends of the gel when placed in said tray nf said plate.

7. The apparatus according to claim 1 wherein said lid means includes a lid extending across said tray and being supported by said side walls and said end walls, said lid means including means for supplying liquid to the interior of said tray and including guide means for guiding vapor bubbles from the interior of said tray through a outlet opening in said lid.

8. The apparatus according to claim 1 including bridge means and means mounting said bridge in said tray between said side walls, said bridge means including a plurality of passages for receiving samples in position to deposit the samples in wells formed in a gel between said bridge means and said platform means.

9. The apparatus according to claim 1 including restraining means for holding a gel in said tray in position on said platform means during electrophoresis and transfer.

10. A method of conducting electrophoresis and subsequent transfer, comprising:
placing a liquid pervious membrane on a liquid pervious platform in a tray;
placing a gel in said tray on said membrane and said platform;
inserting samples in wells formed in the gel;
covering the gel with an electrophoresis buffer;
applying an electric potential through the gel to cause migration of samples in response to the electric potential;
subjecting the gel to depurination solution in the tray;
conducting a denaturation transfer solution through said tray in contact with said gel;
applying a vacuum under said liquid pervious platform, thereby transferring the samples from the gel to the membrane by means of the denaturation transfer solution; and
subsequently removing the membrane from the tray.

11. The method according to claim 10 wherein said samples comprise nucleic acids.

12. The method according to claim 10 comprising the additional step of removing said electrophoresis buffer after applying said electric potential.

13. The method according to claim 12 wherein said electrophoresis buffer is comprised of about 40 mM tris-acetate, pH 8; about 12 mM sodium acetate and about 2 mM EDTA, pH 8.

14. The method according to claim 12 comprising the additional step of removing said depurination solution prior to conducting said denaturation transfer solution through said tray.

15. The method according to claim 14 wherein said depurination solution is comprised of about 0.25 M hydrochloric acid.

16. The method according to claim 12 wherein said denaturation transfer solution is comprised of about 0.5 M sodium hydroxide.

17. The method according to claim 10 wherein said gel is an agarose gel.

18. The method according to claim 10 wherein said membrane is comprised of porous nylon.

19. The method according to claim 10 wherein said liquid pervious platform is comprised of porous polyethylene.

20. Apparatus for transferring nucleic acid fragments from a gel to a support membrane, comprising:
a tray having a bottom wall;
platform means in said tray, said platform means including a porous support plate;
said tray and platform means defining a chamber between said plate and said bottom wall;
liquid reservoir means above said plate, said reservoir means comprising a wall extending above and surrounding the perimeter of said support plate and arranged to contain liquid above said support plate; and
a fluid port communicating with said chamber for withdrawing fluid.

21. The apparatus according to claim 20 wherein said platform means includes guides for positioning the gel when placed on said plate over the membrane.

22. The apparatus according to claim 20 including means for drawing fluid from said chamber means and thereby drawing a vacuum in said chamber means.

23. The apparatus according to claim 20 including electrode means in said tray at opposite sides of said reservoir means for conducting electrophoresis in a gel placed on said plate.

24. A method of conducting the transfer of nucleic acid fragments from a gel to a support membrane, comprising:
placing a liquid pervious membrane on a liquid pervious platform in a tray;
placing a gel in said tray on said membrane and said platform;
placing a transfer solution in the tray in contact with the gel;
applying a vacuum under said liquid pervious platform, thereby transferring the samples from the gel to the membrane by means of the transfer solution, and
subsequently removing the membrane from the tray.

25. The method according to claim 24 wherein the membrane is formed of porous nylon.

26. The method according to claim 24 wherein the platform is formed of porous polyethylene.

* * * * *

Adverse Decesion in Interference

In Interference No. 101,972, involving Patent No. 4,726,889, J. D. Love, M. T. Elliott, P. L. Morgan, PROCESS AND APPARATUS FOR CONDUCTING ELECTROPHORESIS AND TRANSFER, final judgment adverse to the patentee was rendered June 21, 1990 as to claims 1-26.

*[Official Gazette August 28, 1990]*